United States Patent [19]

Gelotte

[11] Patent Number: 4,469,871

[45] Date of Patent: Sep. 4, 1984

[54] PROCESS FOR PREPARING 2-(LOWER-ALKOXY)-1-(PYRIDINYL) ETHENYL LOWER-ALKYL KETONES

[75] Inventor: Karl O. Gelotte, Nassau, N.Y.

[73] Assignee: Sterling Drug Inc., New York, N.Y.

[21] Appl. No.: 471,961

[22] Filed: Mar. 3, 1983

Related U.S. Application Data

[63] Continuation-in-part of Ser. No. 381,162, May 24, 1982, Pat. No. 4,417,054.

[51] Int. Cl.$^3$ .......................................... C07D 211/02
[52] U.S. Cl. ..................................................... 546/249
[58] Field of Search ............................... 546/249, 340

[56] References Cited

U.S. PATENT DOCUMENTS

| | | | |
|---|---|---|---|
| 2,824,121 | 2/1958 | Nicholl et al. | 560/181 |
| 4,223,149 | 9/1980 | Opalka et al. | 546/257 |
| 4,276,293 | 6/1981 | Lesher et al. | 424/248.4 |
| 4,313,951 | 2/1982 | Lesher et al. | 424/263 |
| 4,347,363 | 8/1982 | Singh | 546/249 |
| 4,413,127 | 11/1983 | Singh | 546/249 |

OTHER PUBLICATIONS

Mezheritskii et al., Russian Chemical Reviews 42 (5), 392, 399–402 and 410 (1973).

Primary Examiner—Henry R. Jiles
Assistant Examiner—Bernard Dentz
Attorney, Agent, or Firm—Robert K. Bair; B. Woodrow Wyatt; Paul E. Dupont

[57] ABSTRACT

One aspect of the invention resides in the three step process for preparing cardiotonically active 1,2-dihydro-6-(lower-alkyl)-2-oxo-5-(pyridinyl)nicotinonitriles or 1,2-dihydro-6-(lower-alkyl)-2-oxo-5-(pyridinyl)-nicotinamides which comprises reacting a pyridinylmethyl lower-alkyl ketone with tri-(lower-alkyl) orthoformate, acetic anhydride and acetic acid to produce 2-(lower-alkoxy)-1-(pyridinyl)ethenyl lower-alkyl ketone reacting the latter with cyanoacetamide or malonamide in the presence of a basic condensing agent and neutralizing the reaction mixture, where pyridinyl is 4- or 3-pyridinyl or 4- or 3-pyridinyl having one or two lower-alkyl substituents. Other aspects of the invention reside in the intermediate 2-(lower-alkoxy)-1-(pyridinyl)ethenyl lower-alkyl ketones, their salts and their two step conversion, as described above, to 1,2-dihydro-6-(lower-alkyl)-2-oxo-5-(pyridinyl)-nicotinonitriles or corresponding nicotinamides.

6 Claims, No Drawings

PROCESS FOR PREPARING 2-(LOWER-ALKOXY)-1-(PYRIDINYL) ETHENYL LOWER-ALKYL KETONES

CROSS-REFERENCE TO RELATED APPLICATIONS

This application is a continuation-in-part of copending U.S. patent application Ser. No. 381,162, filed May 24, 1982 now U.S. Pat. No. 4,417,054.

BACKGROUND OF THE INVENTION

1. Field of the Invention

This invention relates to a process for preparing cardiotonically active 1,2-dihydro-6-(lower-alkyl)-2-oxo-5-(pyridinyl)nicotinonitriles and to intermediates used therein.

2. Information Disclosure Statement

Lesher and Philion U.S. Pat. No. 4,313,951, issued Feb. 2, 1982 and based on application Ser. No. 194,461, filed Oct. 20, 1980, in turn a continuation-in-part of its copending application Ser. No. 97,504, filed November 26, 1979 and now abandoned, discloses, inter alia, the process for preparing a 1,2-dihydro-6-(lower-alkyl)-2-oxo-5-(pyridinyl)nicotinonitrile by first reacting a pyridinylmethyl lower-alkyl ketone with dimethylformamide di-(lower-alkyl) acetal to produce a 1-(pyridinyl)-2-(dimethylamino)ethenyl lower-alkyl ketone, then reacting said ketone with cyanoacetamide and acidifying the reaction mixture. The same process is disclosed, inter alia, in Lesher, Opalka and Page U.S. Pat. No. 4,276,293, issued June 30, 1981 and based on application Ser. No. 135,211, filed Mar. 28, 1980.

Opalka and Lesher U.S. Pat. No. 4,223,149, issued Sept. 16, 1980, discloses and claims the process for preparing a 1,2-dihydro-2-oxo-5-(pyridinyl)nicotinonitrile by reacting alpha-(pyridinyl)-beta-[di-(lower-alkyl)amino]-acrolein with malononitrile in a lower-alkanol.

Nicholl et al. U.S. Pat. No. 2,824,121, issued Feb. 18, 1958, discloses and claims an improved process for preparing "oxy alkylidene compounds" using a weakly acid compound as catalytic agent, e.g., zinc chloride, the process being particularly useful in preparing ethoxymethylene malonic diethyl ester by reaction of diethyl malonate and triethyl orthoformate in the presence of acetic anhydride and catalytic amounts of zinc chloride.

Mezheritskii et al., Russian Chemical Reviews 42 (5), 392, 399-402 and 410 (1973), in a review article entitled "The Properties of Orthoesters and Their Applications in Organic Syntheses" has a section (pp. 399-402) re "VIII. Reactions of Orthoesters with Substances Containing An Active Methylene Group". Shown inter alia is the reaction of diethyl malonate with triethyl orthoformate by heating the reactants in the presence of excess acetic anhydride to produce diethyl ethoxymethylenemalonate.

Singh copending U.S. patent application Ser. No. 303,178, filed Sept. 17, 1981, issued Aug. 31, 1982 as U.S. Pat. No. 4,347,363, discloses and claims the process for preparing 1,2-dihydro-6-methyl-2-oxo-5-(pyridinyl)-nicotinonitriles by reacting a pyridinylmethyl methyl ketone with ethoxymethylenemalononitrile.

Singh copending U.S. patent application Ser. No. 381,062, filed May 24, 1982 now U.S. Pat. No. 4,413,127, discloses and claims the process for preparing 1,2-dihydro-6-(lower-alkyl)-2-oxo-5-(pyridinyl)-nicotinonitriles by reacting 2-(lower-alkoxy)-1-pyridinyl)ethenyl lower-alkyl ketone with malononitrile in a lower alkanol.

SUMMARY OF THE INVENTION

The present invention resides in the process for preparing cardiotonically active 1,2-dihydro-6-(lower-alkyl)-2-oxo-5-(pyridinyl)nicotinonitriles or 1,2-dihydro-6-(lower-alkyl)-2-oxo-5-(pyridinyl)nicotinamides by first reacting a pyridinylmethyl lower-alkyl ketone with tri-(lower-alkyl)orthoformate, acetic anhydride and acetic acid to produce 2-(lower-alkoxy)-1-(pyridinyl)ethenyl lower-alkyl ketone, reacting said ketone with cyanoacetamide or malonamide in the presence of a basic condensing agent and neutralizing the reaction mixture. The said substituted nicotinonitriles and nicotinamides produced as above and their cardiotonic use are disclosed, inter alia, in said Lesher and Philion U.S. Pat. No. 4,313,951.

A composition of matter aspect of the invention resides in 2-(lower-alkoxy)-1-(pyridinyl)ethenyl lower-alkyl ketone or salt thereof, which is useful as an intermediate in said process of the invention.

DETAILED DESCRIPTION INCLUSIVE OF PREFERRED EMBODIMENTS

In one of its aspects, the invention resides in the three-step process which comprises reacting pyridinylmethyl lower-alkyl ketone of the formula

with tri-(lower-alkyl)orthoformate, acetic anhydride and acetic acid to produce 2-(lower-alkoxy)-1-(pyridinyl)ethenyl lower-alkyl ketone of formula II,

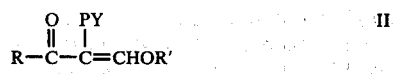

reacting said ketone (II) with cyanoacetamide or malonamide in the presence of a basic condensing agent and neutralizing the reaction mixture to produce 1,2-dihydro-6-R-2-oxo-5-PY-nicotinonitrile or 1,2-dihydro-6-R-2-oxo-5-PY-nicotinamide of formula III,

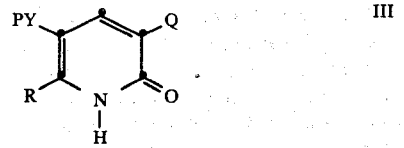

where R and R' are each lower-alkyl, PY is 4- or 3-pyridinyl or 4- or 3-pyridinyl having one or two lower-alkyl substituents, and Q is cyano or carbamyl, respectively. In preferred embodiments 4(or 3)-pyridinylmethyl methyl ketone is first reacted with triethyl or trimethyl orthoformate, acetic anhydride and acetic acid to produce 2-ethoxy(or methoxy)-1-(4- or 3-pyridinyl)ethenyl methyl (or ethyl) ketone, the latter ketone is next reacted with cyanoacetamide in the presence of at least a molar equivalent quantity of alkali hydroxide per mole of cyanoacetamide in a lower-alkanol and then the reaction mixture is neutralized to produce 1,2-dihydro-6-methyl(or ethyl)-2-oxo-5-[4(or 3)-pyridinyl]nicotinonitrile. In a particularly preferred embodiment 4-pyridinylmethyl methyl ketone is first reacted with triethyl orthoformate, acetic anhydride and acetic acid to produce 2-ethoxy-1-(4-pyridinyl)ethenyl methyl ketone, said latter ketone is then reacted with cyanoacetamide in the presence of at least a molar equivalent quantity of sodium hydroxide per mole of cyanoacetamide in methanol, and the reaction mixture is neutralized to produce 1,2-dihydro-6-methyl-2-oxo-5-(4-pyridinyl)nicotinonitrile.

In another of its aspects the invention resides in the process which comprises reacting 2-(lower-alkoxy)-1-(pyridinyl)ethenyl lower-alkyl ketone of formula II with cyanoacetamide or malonamide in the presence of a basic condensing agent and neutralizing the reaction mixture to produce 1,2-dihydro-6-R-2-oxo-5-PY-nicotinonitrile or 1,2-dihydro-6-R-2-oxo-5-PY-nicotinamide of formula III, where R, R', PY and Q have the meanings given for formula III. In preferred embodiments 2-ethoxy(or methoxy)-1-(4- or 3-pyridinyl)ethenyl methyl(or ethyl) ketone is reacted with cyanoacetamide in the presence of at least a molar equivalent quantity of alkali hydroxide per mole of cyanoacetamide in a lower-alkanol, and then the reaction mixture is neutralized to produce 1,2-dihydro-6-methyl(or ethyl)-2-oxo-5-[4(or 3)-pyridinyl]nicotinonitrile. In a particularly preferred embodiment 2-ethoxy-1-(4-pyridinyl)ethenyl methyl ketone is reacted with cyanoacetamide in the presence of at least a molar equivalent quantity of sodium hydroxide per mole of cyanoacetamide in methanol and the reaction mixture is neutralized to produce 1,2-dihydro-6-methyl-2-oxo-5-(4-pyridinyl)nicotinonitrile.

The compounds of formula III are useful as cardiotonic agents, as shown in U.S. Pat. No. 4,313,951, issued Feb. 2, 1982.

A composition of matter aspect of the invention resides in 2-(lower-alkoxy)-1-(pyridinyl)ethenyl lower-alkyl ketone having formula II above or an acid-addition salt thereof, where R and R' are each lower-alkyl and PY is 4- or 3-pyridinyl. Said ketone (II) is useful as an intermediate in the process aspect of the invention given above. Preferred embodiments of this aspect of the invention are the ketones where R is methyl or ethyl, R' is ethyl or methyl, and PY is 4-pyridinyl or 3-pyridinyl. A particularly preferred embodiment is the ketone (II) where R is methyl, R' is ethyl and PY is 4-pyridinyl.

The term "lower-alkyl" as used herein, e.g., as the meaning for R in formula I, II or III or for R' in formula II or as the meaning for one or two substitutents for 4- or 3-pyridinyl, means alkyl radicals having from one to four carbon atoms which can be arranged as straight or branched chains, illustrated by methyl, ethyl, n-propyl, isopropyl, n-butyl, 2-butyl or isobutyl.

The term "lower-alkanol" as used herein, means alkanol having one to four carbon atoms which can be arranged as straight or branched chains, illustrated by methanol, ethanol, n-propanol, 2-propanol, n-butanol, 2-butanol or 2-methyl-n-propanol.

The term "PY" as used herein means 4- or 3-pyridinyl or 4- or 3-pyridinyl having one or two "lower-alkyl" substituents, illustrated by 2-methyl-4-pyridinyl, 3-methyl-4-pyridinyl, 2-methyl-3-pyridinyl, 2,6-dimethyl-4-pyridinyl, 6-methyl-3-pyridinyl (alternatively named 2-methyl-5-pyridinyl), 2,3-dimethyl-4-pyridinyl, 2-ethyl-4-pyridinyl, 2-isopropyl-4-pyridinyl, 2-n-butyl-4-pyridinyl, 2,6-diethyl-4-pyridinyl, 2,6-diisopropyl-4-pyridinyl, and the like.

The compounds of the invention having formula II are useful both in the free base and in the form of acid-addition salts, and both forms are within the purview of the invention. The acid-addition salts are simply a more convenient form for use; and in practice, use of the salt form inherently amounts to use of the base form. The acids which can be used to prepare the acid-addition salts include preferably those which produce, when combined with the free base, pharmaceutically acceptable salts. In practicing the invention, it is convenient to use the free base form or the acetate salt thereof; however, other appropriate pharmaceutically acceptable salts within the scope of the invention are those derived from mineral acids such as hydrochloric acid, sulfuric acid, phosphoric acid and sulfamic acid; and organic acids such as citric acid, lactic acid, tartaric acid, methanesulfonic acid, ethanesulfonic acid, benzenesulfonic acid, p-toluenesulfonic acid, cyclohexylsulfamic acid, quinic acid, and the like, giving the hydrochloride, sulfate, phosphate, sulfamate, citrate, lactate, tartrate, methanesulfonate, ethanesulfonate, benzenesulfonate, p-toluenesulfonate, cyclohexylsulfamate and quinate, respectively.

The acid-addition salts of said compounds of formula II are prepared either by dissolving the free base in aqueous or aqueous-alcohol solution or other suitable solvents containing the appropriate acid and isolating the salt by evaporating the solution, or by reacting the free base and acid in an organic solvent, in which case the salt separates directly or can be obtained by concentration of the solution.

Although pharmaceutically acceptable salts of said compounds of formula II are preferred, all acid-addition salts are within the scope of the invention. All acid-addition salts are useful as sources of the free base form even if the particular salt per se is desired only as an intermediate product as for example when the salt is formed only for purposes of purification or identification, or when it is used as an intermediate in preparing a pharmaceutically acceptable salt by ion exchange procedures.

The molecular structures of the products produced by the process of the invention were assigned on the basis of evidence provided by infrared, nuclear magnetic resonance and mass spectra, by chromatographic mobilities, and by the correspondence of calculated and found values for the elementary analyses for representative examples.

The manner of making and using the instant invention will now be generally described so as to enable a person skilled in the science of medicinal chemistry to make and use the same, as follows:

The process of the invention is carried out by mixing tri-(lower-alkyl) orthoformate, preferably triethyl or trimethyl orthoformate, with (pyridinyl)methyl lower-alkyl ketone (I) and acetic anhydride in acetic acid as solvent. After an exothermic reaction subsides, the reaction mixture is stirred at ambient temperature until completion of the reaction, as determined by tlc analysis, to produce 1-(lower-alkoxy)-2-(pyridinyl)ethenyl lower-alkyl ketone (II). The reaction is run using an excess each of tri-(lower-alkyl)orthoformate, preferably about 1.3 to 1.7 mole per mole of ketone, and acetic anhydride, preferably about 2.0 to 3.0 mole per mole of ketone. The resulting intermediate ketone (II) can be used in the next step of the process without further purification or if desired it can be isolated and further purified. The reaction of II with cyanoacetamide or malonamide to produce 1,2-dihydro-6-(lower-alkyl)-2-oxo-5-(pyridinyl)nicotinonitrile (III, Q is CN) or 1,2-dihydro-6-(lower-alkyl)-2-oxo-5-(pyridinyl)nicotinamide (III, Q is CONH$_2$) is carried out by heating the reactants in a suitable solvent in the presence of at least a molar equivalent of a basic condensing agent per mole of cyanoacetamide or malonamide and then neutralizing the reaction mixture. The reaction using cyanoacetamide is preferably run using as basic condensing agent an alkali hydroxide, preferably sodium hydroxide, either in solid form or in concentrated aqueous solution, in a lower-alkanol, preferably methanol. Optionally and preferably when using malonamide, the reaction also can be run using a lower-alkanol as solvent, preferably methanol or ethanol, and an alkali lower-alkoxide, preferably sodium methoxide or sodium ethoxide, as the basic condensing agent. Other basic condensing agents that can be used include alkali carbonates, e.g., sodium or potassium carbonate, lower-tertiary-amines such as tri-(lower-alkyl)amines, e.g., trimethylamine, triethylamine, benzyldi(lower-alkyl)amines, e.g., benzyldimethylamine, and the like, preferably in aqueous lower-alkanol. Still other basic condensing agents include sodium hydride, lithium diethylamide, lithium diisopropylamide, and the like, which are used in an aprotic solvent, e.g., acetonitrile, benzene, ether, dioxane, tetrahydrofuran, and the like. The neutralization step is carried out by adding a suitable acid, e.g., acetic acid, to the alkaline reaction mixture, preferably to a pH of about 6 to 8.

Advantages of the instant process over the Lesher and Philion prior art process for preparing 1,2-dihydro-6-(lower-alkyl)-5-(pyridinyl)nicotinonitriles and corresponding substituted-nicotinamides inhere in the utilization of less expensive and more readily available starting materials and in the easier production of a pharmaceutically pure product. For example, triethyl orthoformate is much less expensive than dimethylformamide dimethyl acetal and, further, it is much more readily available in the large quantities needed for large-scale or commercial production. Also, an unexpected advantage in the use of 1-(lower-alkoxy)-2-(4-pyridinyl)ethenyl lower-alkyl ketone (II) over the intermediate of the prior art, 1-dimethylamino-2-(4-pyridinyl)ethenyl lower-alkyl ketone, is the greater degree of regioselectivity in the addition of cyanoacetamide to 1-(lower-alkoxy)-2-(4-pyridinyl)ethenyl lower-alkyl ketone. Thus, reaction of cyanoacetamide with 1-ethoxy-2-(4-pyridinyl)ethenyl methyl ketone in place of the prior art intermediate 1-dimethylamino-2-(4-pyridinyl)ethenyl methyl ketone to prepare 1,2-dihydro-6-methyl-2-oxo-5-(4-pyridinyl)nicotinonitrile results in formation of less of the isomeric by-product, 1,2-dihydro-4-methyl-2-oxo-5-(4-pyridinyl)nicotinamide, thereby resulting in a simpler purification procedure required to produce a pharmaceutically pure compound.

Still additional advantages are afforded by the particularly preferred process of preparing 1,2-dihydro-6-methyl-2-oxo-5-(4-pyridinyl)nicotinonitrile by the two step process starting with 4-pyridinylmethyl methyl ketone in the first step to produce 1-(4-pyridinyl)ethenyl methyl ketone and then reacting said ketone in the second step with cyanoacetamide and at least a molar equivalent quantity of sodium hydroxide (either in solid form or in concentrated aqueous solution) in methanol to produce said nicotinonitrile. Thus, the two-step preparation can be conveniently run in one pot without isolating the intermediate 1-(4-pyridinyl)ethenyl methyl ketone. Moreover, the process is more economical in using the inexpensive sodium hydroxide as condensing agent. Also, it eliminates the need to recrystallize the said nicotinonitrile final product from dimethylformamide; and the final product, i.e., 1,2-dihydro-6-methyl-2-oxo-5-(4-pyridinyl)nicotinonitrile, is obtained in an even purer form and in higher yield.

The following examples will further illustrate the invention without, however, limiting it thereto.

A. 1-(LOWER-ALKOXY)-2-(PYRIDINYL)ETHENYL LOWER-ALKYL KETONES

A-1. 1-Ethoxy-2-(4-pyridinyl)ethenyl Methyl Ketone, alternatively named 4-ethoxy-3-(4-pyridinyl)-3-buten-2-one—A 135 g portion (1 m.) of 1-(4-pyridinyl)-propan-2-one was added to 249 ml (1.5 m.) of triethyl orthoformate and 259 ml (2.75 m.) acetic anhydride in 250 ml acetic acid in a 3-neck 2 l. flask. A mild exotherm ensued which carried the temperature from 21° C. to a peak of 56° C. after 30 minutes. The reaction mixture was stirred at room temperature for about 12 to 15 hours or for sufficient time to effect complete reaction as determined by tlc on silica gel with a 3:1 mixture of chloroform/methanol as the mobile phase. The volatiles were removed by distillation under reduced pressure (water aspirator) using a pot temperature of 80° C. Ethanol (200 ml) was added followed by further distillation in vacuo to a pot temperature of 95° C. in order to remove the excess acetic anhydride. (Methanol could be used in place of ethanol.) The residue, 177.8 g deep red oil, consisting primarily of 1-ethoxy-2-(4-pyridinyl)ethenyl methyl ketone, was used directly in the next step (Example B-1) without further purification.

A-2. 1-Ethoxy-2-(4-pyridinyl)ethenyl Methyl Ketone—To a 104.5 g portion (0.77 m.) of 1-(4-pyridinyl)propan-2-one were successively added 141 ml (0.85 m.) of triethylorthoformate, 175 ml (1.86 m.) of acetic anhydride and 200 ml of acetic acid whereupon a exothermic reaction ensued raising the reaction temperature from 23° C. to 49° C. over a 30 minute period. The reaction mixture was then stirred at ambient temperature for about 16 hours and then heated in vacuo to remove the volatile materials. The residue was dissolved in ethyl acetate and the mixture treated with saturated sodium bicarbonate solution until foaming ceased. The organic layer was separated, dried over anhydrous sodium sulfate, treated with decolorizing charcoal and filtered. The filtrate was heated in vacuo to remove the solvent and the residue was swirled with about 300 ml of ether for about 5 minutes whereupon crystallization resulted. The mixture was stirred in an ice bath and the separated solid was collected, washed with cold ether and dried at 45° C. to yield 78.5 g of orange solid. The solid was recrystallized from 200 ml of isopropyl acetate using decolorizing charcoal (5 g). The filtrate obtained after removal of the decolorizing charcoal was cooled whereupon the solid separated. The solid was collected, washed with cold ether and dried in a vacuum oven at 45° C. overnight to yield 63 g of 1-ethoxy-2-(4-pyridinyl)ethenyl methyl ketone, m.p. 84°–88° C.

Acid-addition salts of 1-ethoxy-2-(4-pyridinyl)ethenyl methyl ketone are conveniently prepared by adding to a mixture of 1 g of 1-ethoxy-2-(4-pyridinyl)ethenyl methyl ketone in about 20 ml of methanol the appropriate acid, e.g., hydrochloric acid, methanesulfonic acid, concentrated sulfuric acid, concentrated phosphoric acid, to a pH of about 2 to 3, chilling the mixture after partial evaporation and collecting the precipitated salt, e.g., hydrochloride, methanesulfonate, sulfate, phosphate, respectively.

Following the procedure described in Example A-2 but using in place of triethyl orthoformate a molar equivalent quantity of trimethyl orthoformate or tri-n-propyl orthoformate, it is contemplated that the compounds of Examples A-3 and A-4 can be prepared.

A-3. 1-Methoxy-2-(4-pyridinyl)ethenyl methyl ketone.

A-4. 1-n-Propoxy-2-(4-pyridinyl)ethenyl methyl ketone.

Following the procedure described in Example A-2 but using in place of 1-(4-pyridinyl)propan-2-one a molar equivalent quantity of the appropriate (pyridinyl)methyl lower-alkyl ketone, it is contemplated that there can be obtained the corresponding 1-ethoxy-2-(pyridinyl)ethenyl lower-alkyl ketones of Examples A-5 through A-10.

A-5. 1-Ethoxy-2-(3-pyridinyl)ethenyl methyl ketone, using 1-(3-pyridinyl)propan-2-one.

A-6. 1-Ethoxy-2-(2-methyl-4-pyridinyl)ethenyl methyl ketone, using 1-(2-methyl-4-pyridinyl)propan-2-one.

A-7. 1-Ethoxy-2-(2-ethyl-4-pyridinyl)ethenyl methyl ketone, using 1-(2-ethyl-4-pyridinyl)propan-2-one.

A-8. 1-Ethoxy-2-(2,6-dimethyl-4-pyridinyl)ethenyl methyl ketone, using 1-(2,6-dimethyl-4-pyridinyl)propan-2-one.

A-9. 1-Ethoxy-2-(4-pyridinyl)ethenyl ethyl ketone, using 1-(4-pyridinyl)butan-2-one.

A-10. 1-Ethoxy-2-(4-pyridinyl)ethenyl n-propyl ketone, using 1-(4-pyridinyl)pentan-2-one.

A-11. 1-Ethoxy-2-(4-pyridinyl)ethenyl Ethyl Ketone, 113 g of a dark red oil consisting primarily of said ketone, was prepared following the procedure described in Example A-1 but using 74.5 g of 1-(4-pyridinyl)butan-2-one, 125 ml of triethyl orthoformate, 130 ml of acetic anhydride and 125 ml of glacial acetic acid. The product was used in the next step (Example B-8) without further purification.

B.
1,2-DIHYDRO-6-(LOWER-ALKYL)-2-OXO-5-(PYRIDINYL)NICOTINONITRILES OR 1,2-DIHYDRO-6-(LOWER-ALKYL)-2-OXO-5-(PYRIDINYL)NICOTINAMIDES

B-1. 1,2-Dihydro-6-methyl-2-oxo-5-(4-pyridinyl)-nicotinonitrile—Sodium methylate (189 g 3.5 m.) was added to 2 l. of dry methanol (temperature 60° C.); 105 g (1.25 m.) of cyanoacetamide was added to one portion followed immediately by a solution of 177.8 g (about 1 m.) of 1-ethoxy-2-(4-pyridinyl)ethenyl methyl ketone (from Example A-1) in 500 ml methanol which was also added as quickly as feasible (temperature 55° C.). The reaction mixture was brought to reflux during which time the product began to separate, initially as an almost unstirrable gel; however, upon reaching reflux, the product crystallized into an easily stirred but thick slurry. Refluxing was continued for 1 hour. The reaction was cooled to 55° C. and treated carefully over 5 minutes with 150 ml (2.62 m.) glacial acetic acid (temperature 63° C.). 2 l. methanol was distilled off at atmospheric pressure leaving a thick paste. To the paste was added 2 l. cold water and the pH was adjusted to 6.5–7.0 with 10 ml acetic acid. The reaction mixture was cooled to <5° C. The solid was collected on a funnel, washed with 2×500 ml. cold water, pressed dry and drying continued in a vacuum chamber at 65° C. overnight to yield 147.5 g of a pinkish-tan solid. A 42.2 g portion of this solid was added to 100 ml 8% aqueous NaOH at room temperature. The mixture was stirred until dissolved (5 min.), treated with 4 g of decolorizing charcoal and stirred an additional 5 minutes. The resultant mixture was filtered through a finely divided filter-aid, e.g., cellulose based filter aid (SOLKA FLOC®) or diatomaceous earth. The filtercake was washed with 2×25 ml water and the filtrates combined. The filtrates were treated with 12 ml glacial acetic acid to pH 6.5–7.0. The thick slurry was heated at 90° C. with stirring for 15 minutes to digest (optional). Cooling to <10° C., filtration and water wash with 2×50 ml water affords a pale pink solid. The material was dried in vacuo at 65° C. overnight to yield 41 g pale pink solid (97% recovery). A 37.5 g portion of this solid was dissolved by heating with 200 ml of dimethylformamide, the solution was allowed to cool with stirring to room temperature, cooled in ice and the product was filtered, washed with 2×100 ml ethyl acetate, dried in vacuo at 65° C. overnight to yield as an off-white solid, 34 g (91% recovery) of 1,2-dihydro-6-methyl-2-oxo-5-(4-pyridinyl)nicotinonitrile, m.p. >300° C.

Following the procedure described in Example B-1 but using in place of 1-ethoxy-2-(4-pyridinyl)ethenyl methyl ketone a molar equivalent quantity of the appropriate 1-alkoxy-2-(pyridinyl)ethenyl lower-alkyl ketone, it is contemplated that there can be obtained the corresponding 1,2-dihydro-6-(lower-alkyl)-2-oxo-5-(pyridinyl)nicotinonitriles of Examples B-2 through B-7.

B-2. 1,2-Dihydro-6-methyl-2-oxo-5-(3-pyridinyl)-nicotinonitrile, using 1-ethoxy-2-(3-pyridinyl)ethenyl methyl ketone.

B-3. 1,2-Dihydro-6-methyl-5-(2-methyl-4-pyridinyl-2-oxonicotinonitrile, using 1-ethoxy-2-(2-methyl-4-pyridinyl)ethenyl methyl ketone.

B-4. 5-(2-Ethyl-4-pyridinyl)-1,2-dihydro-6-methyl-2-oxonicotinonitrile, using 1-ethoxy-2-(2-ethyl-4-pyridinyl)ethenyl methyl ketone.

B-5. 1,2-Dihydro-6-methyl-5-(2,6-dimethyl-4-pyridinyl)-2-oxonicotinonitrile, using 1-ethoxy-2-(2,6-dimethyl-4-pyridinyl)ethenyl methyl ketone.

B-6. 1,2-Dihydro-6-n-propyl-5-(4-pyridinyl)-2-oxonicotinonitrile, using 1-ethoxy-2-(4-pyridinyl)ethenyl n-propyl ketone.

B-7. 1,2-dihydro-6-methyl-2-oxo-5-(4-pyridinyl)-nicotinonitrile, using 1-methoxy-2-(4-pyridinyl)ethenyl methyl ketone or 1-(n-propoxy)-2-(4-pyridinyl)ethenyl methyl ketone.

B-8. 6-Ethyl-1,2-dihydro-5-(4-pyridinyl)-2-oxonicotinonitrile, 92 g, m.p. >300° C., was prepared following the procedure described in Example B-1 but using 95 g (1.75 m.) of sodium methoxide, 1 liter of dry methanol, 52.5 g (0.625 m.) of cyanoacetamide, 113 g (0.5 m.) of 1-ethoxy-2-(4-pyridinyl)ethenyl ethyl ketone, a reflux period of one hour, adding 75 ml of glacial acetic acid to the warm reaction mixture, distilling off 1 l. of methanol, adding 1 l. of water, adjusting the pH to 6.5 by adding acetic acid, cooling the mixture in an ice bath, collecting the precipitated product, washing it successively with a little ethanol and then ether, and drying it in a vacuum chamber at 65° C.

Following the procedure described in Example B-1 but using a molar equivalent quantity of malonamide in place of cyanoacetamide and using a molar equivalent of the appropriate 1-alkoxy-2-(pyridinyl)ethenyl lower-alkyl ketone in place of 1-ethoxy-2-(4-pyridinyl)ethenyl methyl ketone or using said ketone, it is contemplated that there can be obtained the corresponding 1,2-dihydro-6-(lower-alkyl)-2-oxo-5-(pyridinyl)nicotinamides of Example E-9 through B-12.

B-9. 1,2-Dihydro-6-methyl-2-oxo-5-(4-pyridinyl)-nicotinamide, using 1-ethoxy-2-(4-pyridinyl)ethenyl methyl ketone.

B-10. 1,2-Dihydro-6-ethyl-2-oxo-5-(4-pyridinyl)-nicotinamide, using 1-ethoxy-2-(4-pyridinyl)ethenyl ethyl ketone.

B-11. 1,2-Dihydro-6-methyl-2-oxo-5-(3-pyridinyl)-nicotinamide, using 1-ethoxy-2-(3-pyridinyl)ethenyl methyl ketone.

B-12. 1,2-Dihydro-6-methyl-2-oxo-5-(2-methyl-4-pyridinyl)nicotinamide, using 1-ethoxy-2-(2-methyl-4-pyridinyl)ethenyl methyl ketone.

B-13. 1,2-Dihydro-6-methyl-2-oxo-5-(4-pyridinyl)-nicotinonitrile—A 30 gallon glass-lined kettle was charged while stirring with 11.2 kg of (186.4 moles) of acetic acid, 12.3 kg (120.6 moles) of acetic anhydride, and 7.32 kg (49.5 moles) of triethyl orthoformate to obtain a clear, colorless solution at 19° C. To the solution was added with stirring 5.24 kg (38.0 moles) of 1-(4-pyridinyl)-2-propanone and a mild exotherm was monitored. After 1½ hour very gentle cooling was applied to maintain a maximum temperature of 50° C. until the exotherm had subsided (1¾ hr.). Stirring at ambient temperature for 17 hours gave a red-orange solution (26° C. final temperature), which was concentrated in vacuo using 60°–70° C. water in the kettle jacket until the reaction volume was reduced to a volume of about 11–12 liters (required 2 hrs.). The concentrate, which contained in solution 1-(4-pyridinyl)ethenyl methyl ketone in the form of its acetate salt, was cautiously diluted with 52 l. of methanol while cooling to 20° C. 2-Cyanoacetamide (4.48 kg, 53.3 moles) was then added, followed by 6.1 l. of 35% aqueous sodium hydroxide solution to reach pH 12. An additional 4.42 l. of 35% aqueous sodium hydroxide solution (53.3 moles) was added and the mixture was heated to reflux for 1 hour (pot temp. 70° C.). After cooling to 50° C., the pH was adjusted to 6.0–6.3 by the addition of 4.6 l. of acetic acid. The mixture was cooled to 0° C. for 15 minutes and filtered on a 28" diameter ceramic vacuum filter. The filter cake was washed with 7.6 l. of cold methanol and then 19 l. of deionized water. It was dried in vacuo at 60° C. affording, as a pink powder, 6.38 kg of 1,2-dihydro-6-methyl-2-oxo-5-(4-pyridinyl)nicotinonitrile (79.4% yield). This product was 99.0–99.5% pure as estimated by tlc. A second crop of 323 g (4% of theoretical yield) was obtained by concentrating the filtrate in vacuo to about one-half the volume, diluting to the original volume with water, then reconcentrating in vacuo to 3/4th volume, and collecting the product. A 6.36 kg portion of the above 6.38 kg of pink powder was further purified as follows. A 30 gallon glass-lined kettle was charged with 17.5 l. of deionized water and 2.81 l. of 35% aqueous sodium hydroxide solution. The 6.36 kg of product was added and the resulting solution was treated at ambient temperature for 15 minutes with 670 g of charcoal. The charcoal was removed by filtration through a finely divided filter-aid, e.g., cellulose based filter aid (SOLKA FLOC®) or diatomaceous earth on an 18" ceramic vacuum filter and the cake was washed with 7.65 l. of deionized water. The filtrate and wash were combined and slowly (over ½ hour) treated with acetic acid (2.16 l. required) to pH 6.5. After stirring at ambient temperature for 45 minutes, the product was collected on a 28" ceramic filter and washed with 15 l. of deionized water. Drying in vacuo at 60° C. overnight gave 6.22 kg of off-white product, 1,2-dihydro-6-methyl-2-oxo-5-(4-pyridinyl)nicotinonitrile, m.p. >300° C., (6.22/6.36=97.8% recovery).

B.14. 1,2-Dihydro-6-methyl-2-oxo-5-(4-pyridinyl)-nicotinonitrile—To a solution containing 2.6 g of sodium hydroxide pellets dissolved in 41 ml of methanol was added 2.5 g of cyanoacetamide with stirring. After dissolution was complete (about 5 minutes), to the solution was added a solution containing 5.0 g of 1-(4-pyridinyl)ethenyl methyl ketone in 15 ml of methanol and the reaction mixture was heated to reflux for one hour, cooled to 50° C. and treated with 4.2 ml of acetic acid. The methanol was distilled off at atmospheric pressure and the residue treated with 55 ml of water. Since the pH was 6.0, there was no need to adjust it. The mixture was cooled to 5° C. and the separated solid was collected, washed successively with 50 ml portions of cold water, ethanol and ether, and air-dried to produce 4.7 g (85.5% yield) of 1,2-dihydro-6-methyl-2-oxo-5-(4-pyridinyl)nicotinonitrile, m.p. >300° C.

Following the procedure described in Example B-14 but using in place of 1-ethoxy-2-(4-pyridinyl)ethenyl methyl ketone a molar equivalent quantity of the appropriate 1-alkoxy-2-(pyridinyl)ethenyl lower-alkyl ketone, it is contemplated that there can be obtained the corresponding 1,2-dihydro-6-(lower-alkyl)-2-oxo-5-(pyridinyl)nicotinonitriles of Examples B-15 through B-20.

B-15. 1,2-Dihydro-6-methyl-2-oxo-5-(3-pyridinyl)-nicotinonitrile, using 1-ethoxy-2-(3-pyridinyl)ethenyl methyl ketone.

B-16. 1,2-Dihydro-6-methyl-5-(2-methyl-4-pyridinyl)-2-oxonicotinonitrile, using 1-ethoxy-2-(2-methyl-4-pyridinyl)ethenyl methyl ketone.

B-17. 5-(2-Ethyl-4-pyridinyl)-1,2-dihydro-6-methyl-2-oxonicotinonitrile, using 1-ethoxy-2-(2-ethyl-4-pyridinyl)ethenyl methyl ketone.

B-18. 1,2-Dihydro-6-methyl-5-(2,6-dimethyl-4-pyridinyl)-2-oxonicotinonitrile, using 1-ethoxy-2-(2,6-dimethyl-4-pyridinyl)ethenyl methyl ketone.

B-19. 1,2-Dihydro-6-n-propyl-5-(4-pyridinyl)-2-oxonicotinonitrile, using 1-ethoxy-2-(4-pyridinyl)ethenyl n-propyl ketone.

B-20. 1,2-dihydro-6-methyl-2-oxo-5-(4-pyridinyl)-nicotinonitrile, using 1-methoxy-2-(4-pyridinyl)ethenyl methyl ketone or 1-(n-propoxy)-2-(4-pyridinyl)ethenyl methyl ketone.

I claim:

1. The process which comprises reacting pyridinylmethyl lower-alkyl ketone of the formula

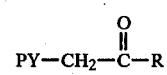

with tri-(lower-alkyl) orthoformate, acetic anhydride and acetic acid to produce 2-(lower-alkoxy)-1-(pyridinyl)ethenyl lower-alkyl ketone of the formula

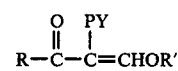

reacting said ketone with cyanoacetamide or malonamide in the presence of a basic condensing agent and neutralizing the reaction mixture to produce 1,2-dihydro-6-R-2-oxo-5-PY-nicotinonitrile or 1,2-dihydro-6-R-2-oxo-5-PY-nicotinamide of the formula

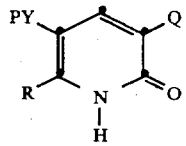

where R and R' are each lower-alkyl, PY is 4- or 3-pyridinyl or 4- or 3-pyridinyl having one or two lower-alkyl substituents and Q is cyano or carbamyl.

2. The process according to claim 1 where 4(or 3)-pyridinylmethyl methyl(or ethyl) ketone is first reacted with triethyl or trimethyl orthoformate, acetic anhydride and acetic acid to produce 2-(ethoxy or methoxy)-1-(4- or 3-pyridinyl)ethenyl methyl(or ethyl) ketone, the latter ketone is next reacted with cyanoacetamide in the presence of at least a molar equivalent quantity of alkali hydroxide per mole of cyanoacetamide in a lower alkanol and then the reaction mixture is neutralized to produce 1,2-dihydro-6-methyl(or ethyl)-2-oxo-5-[4(or 3)-pyridinyl]nicotinonitrile.

3. The process according to claim 2 where 4-pyridinylmethyl methyl ketone is first reacted with triethyl orthoformate, acetic anhydride and acetic acid to produce 2-ethoxy-1-(4-pyridinyl)ethenyl methyl ketone, said latter ketone is reacted with cyanoacetamide in the presence of at least a molar equivalent quantity of sodium hydroxide per mole of cyanoacetamide in methanol and the reaction mixture is neutralized to produce 1,2-dihydro-6-methyl-2-oxo-5-(4-pyridinyl)nicotinonitrile.

4. The process which comprises reacting 2-(lower-alkoxy)-1-(pyridinyl)ethenyl lower-alkyl ketone of the formula

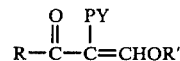

with cyanoacetamide or malonamide in the presence of a basic condensing agent and neutralizing the reaction mixture to produce 1,2-dihydro-6-R-2-oxo-5-PY-nicotinonitrile or 1,2-dihydro-6-R-2-oxo-5-PY-nicotinamide of the formula

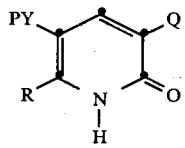

where R and R' are each lower-alkyl, PY is 4- or 3-pyridinyl or 4- or 3-pyridinyl having one or two lower-alkyl substituents and Q is cyano or carbamyl.

5. The process according to claim 4 where 2-(ethoxy or methoxy)-1-(4- or 3-pyridinyl)ethenyl methyl(or ethyl) ketone is reacted with cyanoacetamide in the presence of at least a molar equivalent quantity of alkali hydroxide per mole of cyanoacetamide in a lower alkanol and then the reaction mixture is neutralized to produce 1,2-dihydro-6-methyl(or ethyl)-2-oxo-5-[4(or 3)-pyridinyl]nicotinonitrile.

6. The process according to claim 4 where 2-ethoxy-1-(4-pyridinyl)ethenyl methyl ketone is reacted with cyanoacetamide in the presence of at least a molar equivalent quantity of sodium hydroxide per mole of cyanoacetamide in methanol and the reaction mixture is neutralized to produce 1,2-dihydro-6-methyl-2-oxo-5-(4-pyridinyl)nicotinonitrile.

* * * * *

UNITED STATES PATENT AND TRADEMARK OFFICE
CERTIFICATE OF CORRECTION

PATENT NO. : 4,469,871

DATED : September 4, 1984

INVENTOR(S) : Karl O. Gelotte

It is certified that error appears in the above-identified patent and that said Letters Patent is hereby corrected as shown below:

The numerals "1" and "2", defining the positions of the alkoxy and pyridinyl substituents, respectively, in the names of the ketones of formula II should be interchanged at the following places of the printed patent:

Column 4, line 60

Column 5, lines 42 and 48

Column 6, lines 12, 14, 32, 35, 61, 63 and 65

Column 7, lines 10, 12, 18, 21, 23, 26, 28, 31, 33, 35 and 54

Column 8, lines 27, 29, 35, 38, 41, 44, 47, 50, 51 and 58

Column 9, lines 1, 2, 8, 11, 15 and 17

Column 10, lines 27, 29, 35, 38, 41, 44, 47, 50 and 51.

At column 5, lines 44 and 50, "1-dimethylamino-2-(4-pyridinyl)ethenyl" should read --2-dimethylamino-1-(4-pyridinyl)-ethenyl--.

At column 9, line 35, and column 10, lines 13-14, "1-(4-pyridinyl)ethenyl" should read --2-ethoxy-1-(4-pyridinyl)-ethenyl--.

Signed and Sealed this

Twenty-fourth Day of February, 1987

Attest:

DONALD J. QUIGG

*Attesting Officer*  *Commissioner of Patents and Trademarks*